(12) United States Patent
Tham et al.

(10) Patent No.: US 9,744,321 B2
(45) Date of Patent: Aug. 29, 2017

(54) SYSTEM AND METHOD OF DETECTING INTEGRITY OF BREATHING SYSTEMS FOR SAFE AND OPTIMAL DELIVERY

(71) Applicant: General Electric Company, Schenectady, NY (US)

(72) Inventors: Robert Q. Tham, Madison, WI (US); Julie Anne Mills, Monona, WI (US); Mike Foulis, Madison, WI (US)

(73) Assignee: General Electric Company, Schenectady, NY (US)

( * ) Notice: Subject to any disclaimer, the term of this patent is extended or adjusted under 35 U.S.C. 154(b) by 783 days.

(21) Appl. No.: 14/107,883

(22) Filed: Dec. 16, 2013

(65) Prior Publication Data

US 2015/0165142 A1    Jun. 18, 2015

(51) Int. Cl.
*A61M 16/00* (2006.01)
*A61M 16/08* (2006.01)
*A61M 16/10* (2006.01)

(52) U.S. Cl.
CPC ........ *A61M 16/0051* (2013.01); *A61M 16/08* (2013.01); *A61M 16/0816* (2013.01); *A61M 16/0875* (2013.01); *A61M 16/0883* (2014.02); *A61M 16/1055* (2013.01); *A61M 16/1065* (2014.02); *A61M 2205/14* (2013.01); *A61M 2205/3317* (2013.01); *A61M 2205/3592* (2013.01); *A61M 2205/6018* (2013.01); *A61M 2205/6054* (2013.01)

(58) Field of Classification Search
CPC .......... A61M 16/0051; A61M 16/0875; A61M 16/08; A61M 16/0816; A61M 16/0883; A61M 2205/6054; A61M 16/1065; A61M 16/1055; A61M 2205/6018; A61M 2205/14; A61M 2205/3592; A61M 2205/3317

See application file for complete search history.

(56) References Cited

U.S. PATENT DOCUMENTS

| 5,604,681 | A | 2/1997 | Koeninger |
| 6,649,829 | B2 | 11/2003 | Garber et al. |
| 6,897,374 | B2 | 5/2005 | Garber et al. |
| 7,348,875 | B2 | 3/2008 | Hughes et al. |

(Continued)

FOREIGN PATENT DOCUMENTS

| EP | 1632456 | 3/2006 |
| WO | 2007106486 | 9/2007 |

OTHER PUBLICATIONS

International Search Report and Written Opinion from Corresponding PCT application No. PCT/US2014/055740 mailed Dec. 19, 2014; 11 pages.

*Primary Examiner* — Steven Douglas
(74) *Attorney, Agent, or Firm* — Andrus Intellectual Property Law, LLP

(57) ABSTRACT

A system and to automate the integrity check of a breathing system and inform a ventilator to deliver a compensated gas volume, and alert the user if a vital component of a breathing circuit is absent or not fully connected. The system and method utilize an open RFID tag on a first point of connection and a conducting ring on the second point of connection such that when a circuit connection is made, the open RFID tag becomes active and provides an RFID reader with data regarding the circuit connection.

18 Claims, 5 Drawing Sheets

(56) References Cited

U.S. PATENT DOCUMENTS

| | | |
|---|---|---|
| 7,394,375 B2 | 7/2008 | Johnson |
| 7,396,995 B2 | 7/2008 | Laurent et al. |
| 7,443,296 B2 | 10/2008 | Mezhinsky et al. |
| 7,647,954 B2 | 1/2010 | Garber et al. |
| 7,841,357 B2 | 11/2010 | Rankin |
| 7,954,374 B2 | 6/2011 | Rankin |
| 2001/0017134 A1 | 8/2001 | Bahr |
| 2005/0211761 A1 | 9/2005 | Anttila et al. |
| 2006/0278221 A1 | 12/2006 | Schermeier et al. |
| 2006/0283447 A1* | 12/2006 | Dhuper ................ A61M 16/08 128/203.12 |
| 2007/0265877 A1 | 11/2007 | Rice et al. |
| 2007/0277824 A1 | 12/2007 | Aylsworth et al. |
| 2011/0001611 A1 | 1/2011 | Schermeier et al. |
| 2011/0004276 A1* | 1/2011 | Blair .................... A61B 5/0002 607/60 |
| 2012/0185267 A1* | 7/2012 | Kamen ................ G06Q 50/22 705/2 |
| 2012/0204874 A1 | 8/2012 | Sofranko |
| 2012/0229272 A1 | 9/2012 | Jacob et al. |

\* cited by examiner

SYSTEM AND METHOD OF DETECTING INTEGRITY OF BREATHING SYSTEMS FOR SAFE AND OPTIMAL DELIVERY

FIELD

The present application is directed to the field of patient ventilators. More specifically, the present application is directed to ventilator circuit integrity detection.

BACKGROUND

It is desirable that, prior to the start or restart of ventilation to a patient requiring respiration assistance, that the integrity of the circuit be validated. This includes that the circuit is intact, connected, and the right patient interface component is attached. This will assure that the ventilator delivers the appropriate set of breathing gases without gas leakage. It is also advantageous that a humidifier and bacteria filter be attached to ensure gases breathed by the patient are humidified and cross contamination is prevented. In volume controlled ventilation, some gas volumes delivered by the ventilator is absorbed in a compliant breathing circuit, or circuit component such as a humidifier, filters, HME, resulting in less tidal volume delivered to the patient. Breathing circuits come in different lengths with correspondingly different compliance values. Present methods to compensate gas volume losses is to inject a known gas volume and measure the total circuit compliance prior to the start of ventilation, or enter the type of circuit elements with their compliances or predefined compliances summing them together to obtain the total compliance. These are tedious and require additional steps by the user to enter the right information, enter the total circuit compliance and compensate for the volumes not delivered to the patient.

Current solutions detect circuit disconnects by detecting gas leakage or failure to pressurize the breathing circuit during ventilation. A common approach to detect disconnects in other industries is to provide a parallel loop back connection to test the integrity of the connected circuit. Loop-back connection can be done via electrical, pneumatic or optical leads that run the length of the breathing circuit. A weakness in this solution is it does not report what is connected and where. The introduction of electrical wires, tubes or optical fiber glass running along the gas flow passage of the breathing circuit components can be costly and intrusive. Another weakness, particularly in anesthesia ventilation, is the failure to detect reconnection of the breathing circuit. A test procedure must be conducted prior to start of ventilation to compute total compliance and resistance to provide compensation for compliance and resistance losses. This is time consuming and has to be added to the user workflow.

SUMMARY

The above-mentioned shortcomings, disadvantages and problems are addressed herein which will be understood by reading and understanding the following specification.

The system and method of the present application automates the integrity check of the breathing system and informs the ventilator to deliver the compensated gas volume, and alert the user if a vital component of breathing circuit is absent or not fully connected. The present application utilizes an open RFID tag on a first point of connection and a conducting ring on the second point of connection such that when a circuit connection is made, the open RFID tag becomes active and provides an RFID reader with data regarding the circuit connection.

In one aspect of the present application, a ventilator breathing circuit comprises a plurality of circuit connections, each of the plurality of circuit connections including a first conduit and a second conduit, a radio frequency identification (RFID) reader, an open RFID tag affixed to any of the first conduits, a conducting ring affixed to the second conduit corresponding to the first conduit having the open RFID tag, such that when the first conduit and the second conduit are connected, the open RFID tag is activated and sends a set of data to the RFID reader, wherein the set of data includes information about the circuit connection.

In another aspect of the present application, a method of monitoring the integrity of a ventilator breathing circuit, the method comprises identifying a circuit connection of a ventilator breathing circuit, fashioning a first conduit of the circuit connection with an open RFID tag, fashioning a second conduit of the circuit connection with a conducting ring, connecting the first and second conduits of the identified circuit connection, thus activating the open RFID tag, receiving a set of data from the identified circuit connection, and analyzing the set of data from the identified circuit connection, optimizing the ventilation delivery based on the analysis, and displaying the analysis and the optimization for a user.

In another aspect of the present application, a non-transitory computer-readable medium includes instructions that, when executed on a computing system, cause the computing system to receive a set of data from a circuit connection wherein an open RFID tag is activated by a conducting ring when a connection is made between a first and second conduit, analyze the set of data from the circuit connection, optimize a delivery of the ventilator based on the analysis, and display the analysis and the optimization for a user.

DETAILED DESCRIPTION

In the present description, certain terms have been used for brevity, clearness and understanding. No unnecessary limitations are to be applied therefrom beyond the requirement of the prior art because such terms are used for descriptive purposes only and are intended to be broadly construed. The different systems and methods described herein may be used alone or in combination with other systems and methods. Various equivalents, alternatives and modifications are possible within the scope of the appended claims. Each limitation in the appended claims is intended to invoke interpretation under 35 U.S.C. §112, sixth paragraph, only if the terms "means for" or "step for" are explicitly recited in the respective limitation.

In the following detailed description, reference is made to the accompanying drawings that form a part hereof, and in which is shown by way of illustration specific embodiments that may be practiced. These embodiments are described in sufficient detail to enable those skilled in the art to practice the embodiments, and it is to be understood that other embodiments may be utilized and that logical, mechanical, electrical and other changes may be made without departing from the scope of the embodiments. The following detailed description is, therefore, not to be taken as limiting the scope of the invention.

Figure 1:
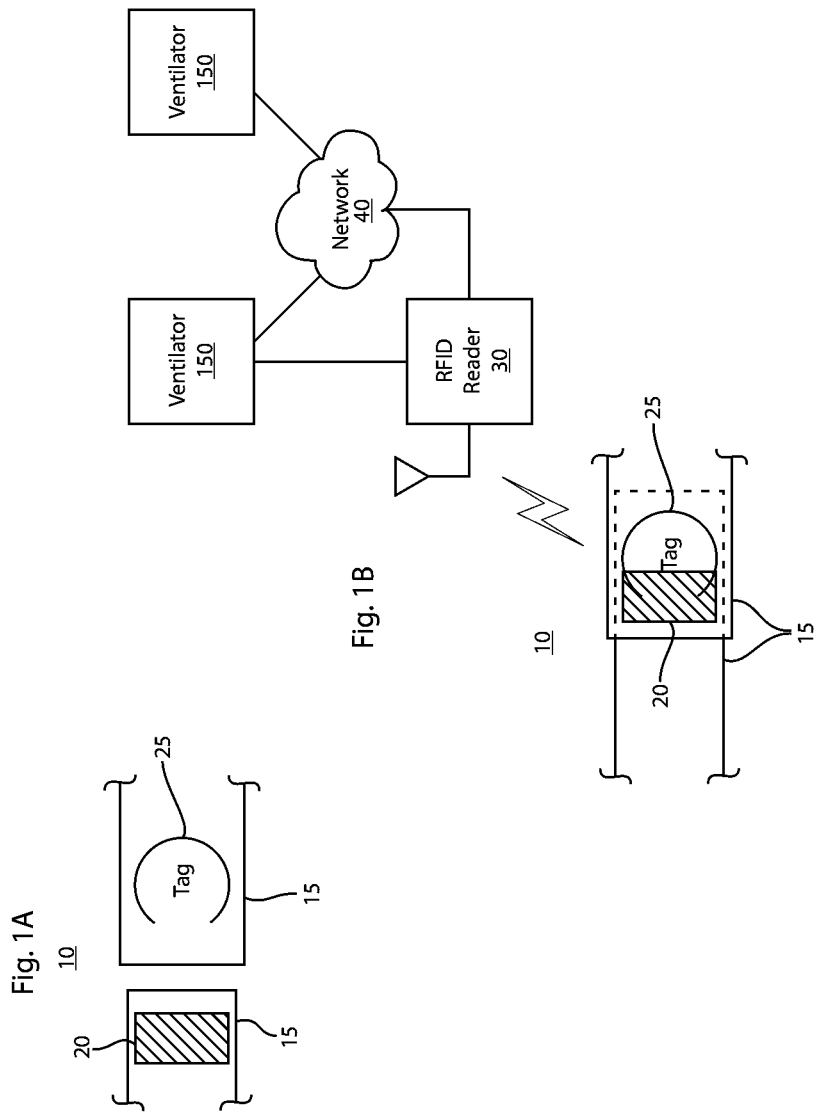
FIGS. 1a and b are schematic illustrations of a circuit connection and network in accordance with an exemplary embodiment of the present application.
Figure 2:
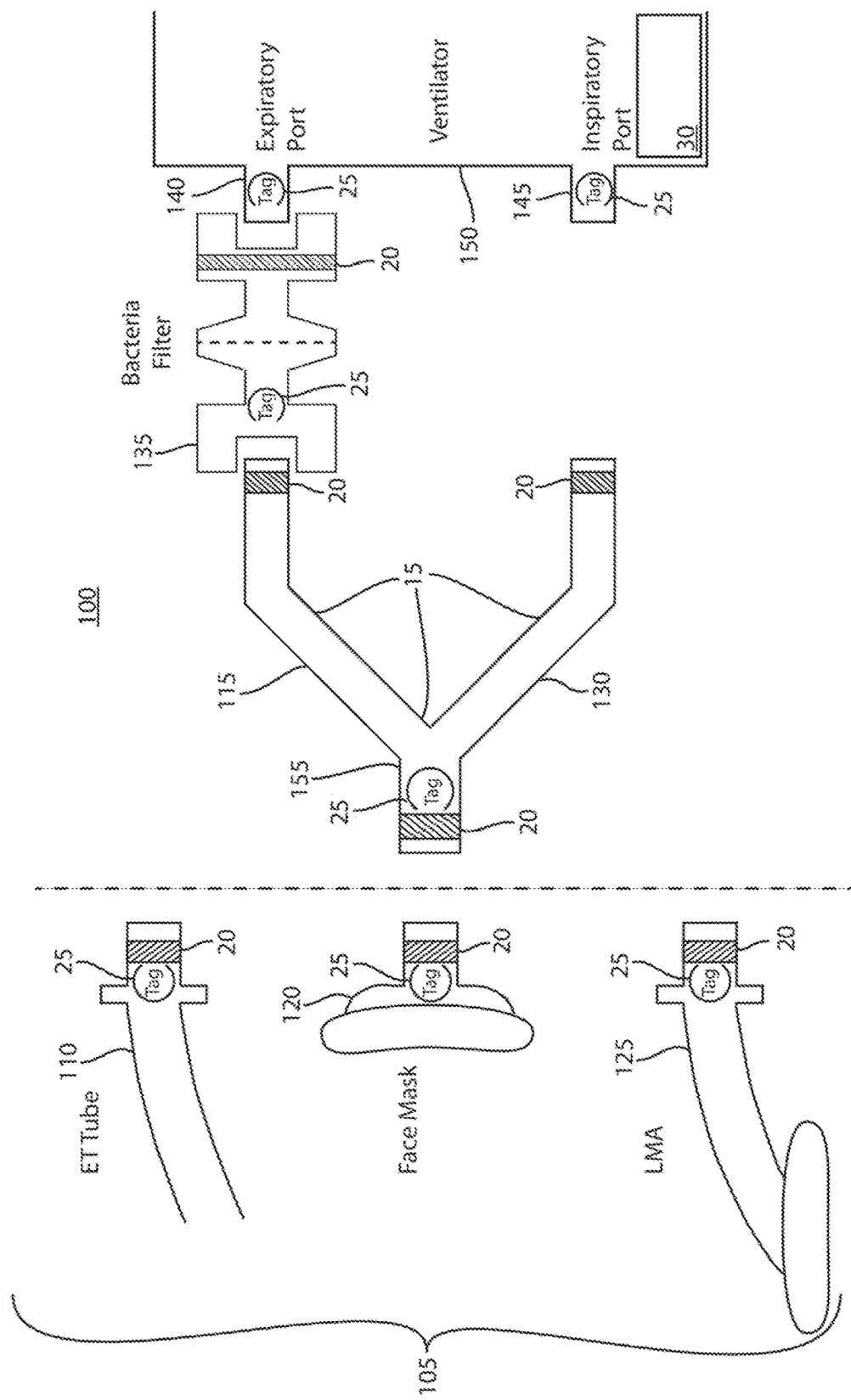
FIG. 2 is a schematic illustration of a breathing circuit illustrating an embodiment of the present application.

Referring to FIGS. 1a, 1b and 2, the system and method of the present application makes use of open radio frequency identification (RFID) tags 25 located at the opening of circuit components 135 to detect the connection of two breathing circuit components 135 or any circuit connection 10. In one embodiment, an open RFID circuit tag 25 (having an open lead to the antenna wire or the RFID chip) is utilized such that the RFID chip in the open RFID tag 25 is not communicating when the circuit connection 10 is open, such as is illustrated in FIG. 1a. When connected, the open lead of the open RFID tag 25 connects with a conducting ring 20 to complete the electrical connection, thus resulting in an active RFID tag 27, as illustrated in FIG. 1b. Once connected, the active RFID tag 27 behaves as a conventional RFID tag and may be energized by an RFID reader to send and receive signals to communicate their presence and data to an RFID reader 30 as an active connection 10 and to report properties, if any. Properties can include device type such as bacteria filter, number of connecting ports or circuit connections 10, connecting location, physical property of the component, such as compliance and flow resistance, that are relevant to safe and optimal ventilation delivery. Simultaneous reporting of active RFID tags 27 can provide the location and sequence of the circuit connections 10. This helps to map the topology of active portions of the breathing circuit 100 (FIG. 2). Since only active circuit connections 10 are energized and can communicate with the RFID reader 30, only active circuit connections 10 can report to the RFID reader 30. The RFID reader 30 is typically located proximal to the ventilator 150 and/or electronically connected with the ventilator 150 computing system 300. The RFID reader 30 detects the presence of active RFID tags 27 and reads all the circuit connections 10 that are actively connected together. It then forwards the results to the computing system 300 that confirms the breathing circuit 100 is intact, the required circuit components 135 such as a filter or HME are present, and the physical properties of the breathing circuit 100, for example, total resistance and compliance of each component present to yield the total resistance and compliance of the breathing circuit. An alarm is raised if a critical safety component 135, for example a bacteria filter 135 is not actively connected to the breathing circuit 100 prior to start of ventilation. The controller 300 can be programmed to deny the start of ventilation until a critical circuit component 135 is connected or the denial overridden by the user. During ventilation delivery, the ventilator 150 uses the aggregated physical makeup of the circuit components 135 to adjust tidal volume delivery to compensate for gas volumes retained in the circuit components 135 (resulting in compliant volumes losses, dead spaces and other issues) that is not delivered to the patient. Similar compensation can be provided to compensate for flow resistance in the gas passage of the breathing circuit 100. Additional information can be gleaned from computing frequency, duration of active use of a connected circuit components 135, such as to replace a circuit component 135.

Referring back to FIG. 1a, a circuit connection 10 of the present application is illustrated in an unconnected position. In other words, the two breathing circuit conduits 15 are not connected to one another, leaving the open RFID tag 25 in a non-energized state that does not allow the open RFID tag 25 to transmit a set of data to the RFID reader 30. As discussed previously, the open RFID tag 25 includes information regarding the breathing circuit conduit 15 that it is connected to, such as but not limited to, the location of the breathing circuit conduit 15 in the breathing circuit 100 and the particular circuit component 135 that the breathing circuit conduit 15 may be associated with or connected to. The conducting ring 20 is configured on the opposite breathing circuit conduit 15, and when the circuit connection 10 is in a connected position as shown in FIG. 1b, the conducting ring 20 completes the circuit so that the active RFID tag 27 is able to transmit a set of data to the RFID reader 30.

As discussed previously, the RFID reader 30 may be configured proximate to the breathing circuit 100, and the ventilator 150, and/or connected through a network 40 or hardwired to a computing system 300 as further illustrated in FIG. 1b, and further described below with respect to FIG. 5.

Referring now to FIG. 2, an embodiment of a breathing circuit 100 of the present application is illustrated. Here, a ventilator 150 including an expiratory port 140 and an inspiratory port 145 are connected with breathing circuit conduits 15 to any one of a patient interface component 105 in order to provide ventilation to a patient (not shown). The ventilator 150 further includes an RFID reader 30 as discussed above, but it should be noted that not all ventilators will have such an RFID reader 30. The breathing circuit 100 also includes various circuit components 135, in this case a bacteria filter is illustrated but should not limit the present application to such a filter. Any other appropriate filters or devices that belong in breathing circuits 100 may be connected through the breathing circuit 100 such as, but not limited to, heat moisture exchanges, active humidifiers and nebulizers. The breathing circuit 100 also includes an expiratory limb 115 and an inspiratory limb 130, as well as a y-piece 155, as is well known in the art. The patient interface components 105 may include any patient interface components known in the art, and illustrated are an endotracheal tube 110, a facemask 120, and a laryngeal mask 125.

Still referring to FIG. 2, in this embodiment the inspiratory limb 130 and expiratory limb 115 are configured with conducting rings 20 on the ends of the limbs 115, 130 in close proximity to the ventilator 150. Furthermore, the y-piece 155 includes both a conducting ring 20 and an open RFID tag 25 on the breathing circuit conduit 15 portion to be connected with any of the patient interface components 105. Each of the patient interface components 105 is configured with a conducting ring and open RFID tag 25. The circuit component 135, in this case a bacteria filter, includes a conducting ring 20 on the end proximate to the expiratory port 140 of the ventilator 150, and an open RFID tag 25 on the end configured proximate to the expiratory limb 115. The expiratory port 140 and the inspiratory port 145 both include open RFID tags 25.

Still referring to FIG. 2, when each connection is made in this embodiment, and the open RFID tags 25 become active RFID tags 27 (FIG. 1b), thus energized by the completion of the RFID tag 27 circuit with a conducting ring 20, the active RFID tags 27 will communicate with the RFID reader 30 in order to provide a set of data to the RFID reader 30 that includes its device type, its properties, number of connecting parts, location of the active RFID tag 27, a status that the active RFID tag 27 is indeed connected, and further whether the active RFID tag 27 is associated with any circuit component 135. For example, when the y-piece 155 is connected to the endotracheal tube 110, the active RFID tag 27 on the y-piece 155 will transfer a set of data to the RFID reader 30 that indicates that the y-piece 155 is connected. The endotracheal tube 110 will also send a signal from its active RFID tag 27 that it is further connected. A user will then know that the endotracheal tube 110 is connected to the y-piece 155, and that that portion of the breathing circuit 100 has an acceptable integrity. It should first be noted that the Applicant has illustrated the breathing circuit 100 in FIG. 2 (and in FIG. 3) to show all of the open RFID tags 25 and conducting rings 20 in an unconnected state for clarity. Again for clarity, these connections have only been shown in FIG. 1b. It should be assumed that the breathing circuit 100 of FIGS. 2 and 3, when connected, will include circuit connections 10 in every location where circuit connections 10 are to be made. Of course, some circuit connections 10 in the breathing circuit 100 of FIGS. 2 and 3 will include two conducting rings 20 and two active RFID tags 27 in the instances where each breathing circuit conduit 15 includes an open RFID tag 25 and a conducting ring 20.

It should be further noted that in this embodiment, the ends of the expiratory and inspiratory limbs 115, 130 proximate to the ventilator 150 do not include open RFID tags 25, and only conducting rings 20. In this case, only the position and connectivity of the circuit component 135 (bacteria filter), expiratory port 140 and inspiratory port 145 will be transmitted to the RFID reader 30 when all of these circuit connections 10 are made. When the number of available open RFID tags 25 before connection of the breathing circuit 100 matches the number of active RFID tags 27 after the breathing circuit 100 is connected, then the breathing circuit 100 is completed and connected. After connection, the active RFID tags 27 continue to communicate with the RFID reader 30. Any subsequent circuit connection 10 disconnect may be recognized by the RFID reader 30 when a previously active RFID tag 27 fails to continue to report and deliver a set of data to the RFID reader 30 during any given read cycle.

Figure 3:
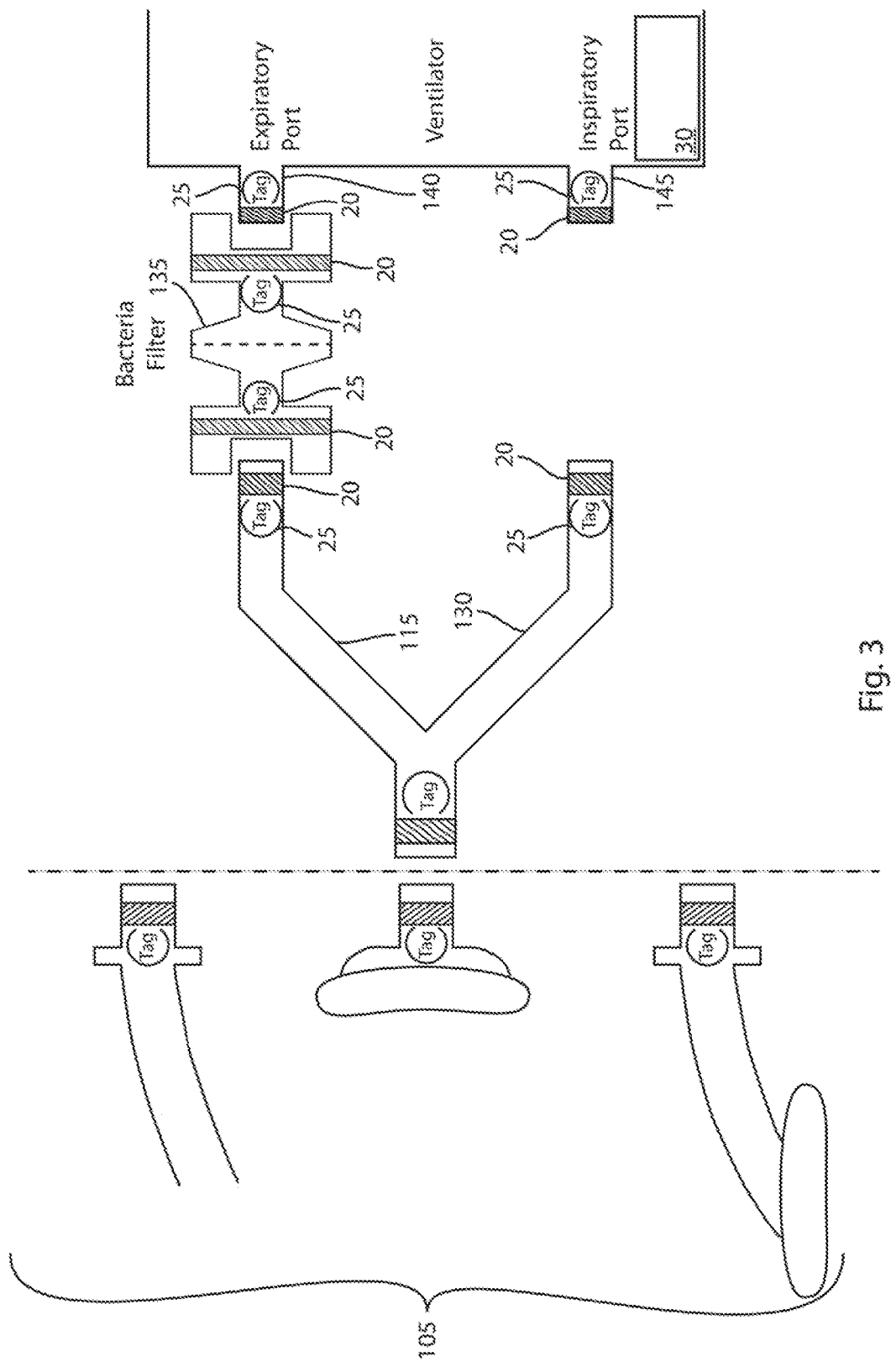
FIG. 3 is a schematic illustration of a breathing circuit illustrating an embodiment of the present application.

Referring now to FIG. 3 of the present application, an additional embodiment showing both open RFID tags 25 and conducting rings 20 on each and every connection point 16 of the breathing circuit 100 is illustrated. For ease of description, only the pertinent portions of FIG. 3 have been labeled with numerals, and it can be assumed that those components not labeled in FIG. 3 have the same number as its corresponding component in FIG. 2. Here, as an example, the inspiratory limb 130 includes an open RFID tag 25 and a conducting ring 20, as does the inspiratory port 145. When this circuit connection 10 is made, both the inspiratory limb 130 RFID tag 25 and the inspiratory port 145 open RFID tag 25 will become active RFID tags 27 and send a set of data reflecting the conduit 15, conduit location of the circuit component 135, and location and connectivity of each of the inspiratory limb 130 and inspiratory port 145 to the RFID reader 30. This embodiment, by way of including an open RFID tag 25 and conducting ring 20, at each and every connection point in the breathing circuit 100, ensures the highest level of integrity and tracking of the breathing circuit 100 that is possible. Of course, a user may be able to customize the breathing circuit 100 solution by including open RFID tags 25 and conducting rings 20 on those connection points. One advantage of knowing the pairing of all of the circuit component 135 conduits 15 and the location for each circuit component 135 conduit 15, the arrangement of the entire breathing circuit 100 can be mapped out via the connected sequence of the circuit connections 10.

Figure 4:
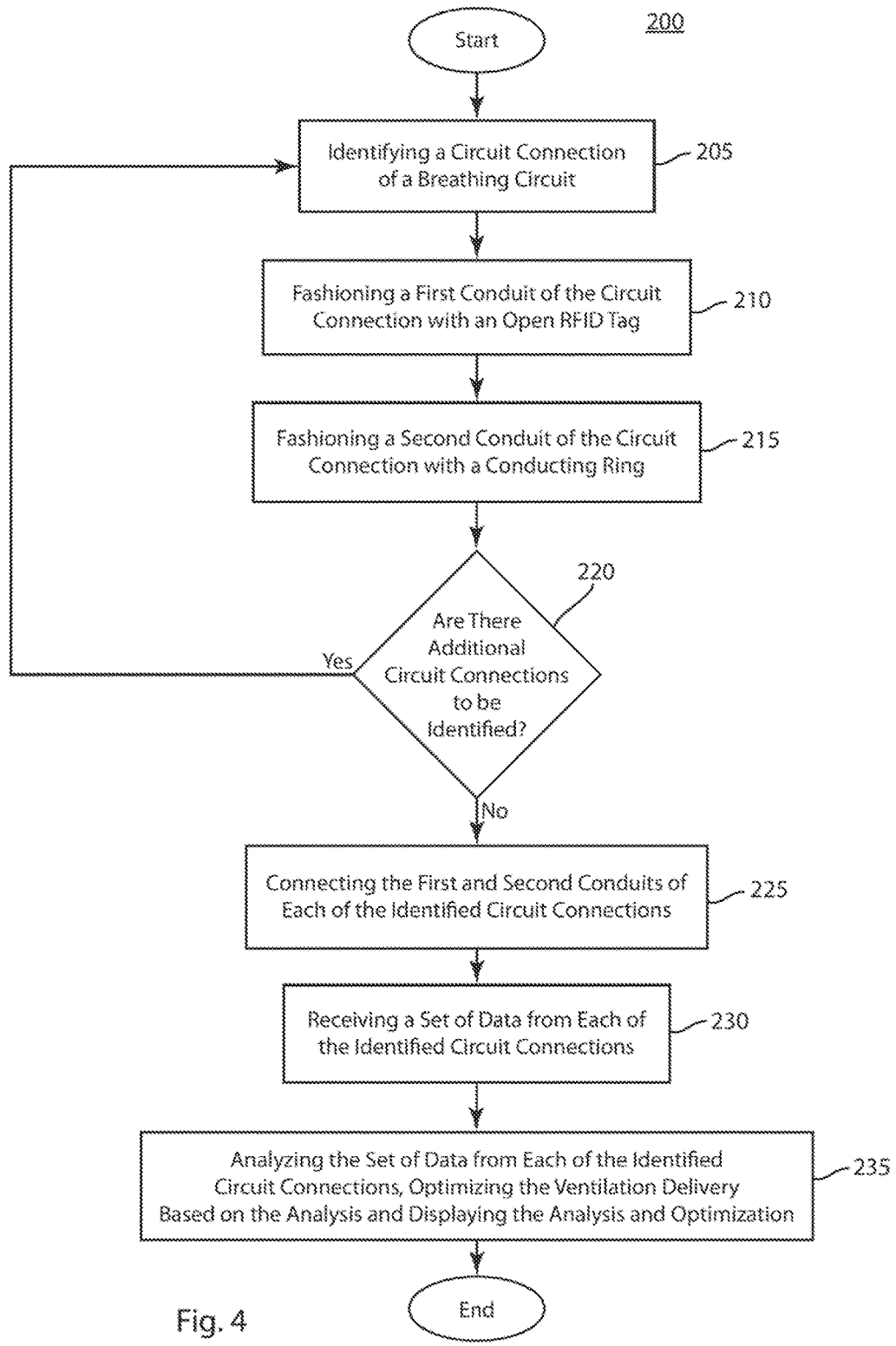
FIG. 4 is a flow chart illustrating an exemplary method in accordance with an embodiment of the present application.

Referring now to FIG. 4, a method 200 of the present application is illustrated in the flowchart. In step 205, a user identifies a circuit connection of a breathing circuit, and in step 210 a first conduit of the identified circuit connection is fashioned with an open RFID tag. In step 215, a second conduit of the identified circuit connection is fashioned with a conducting ring. If there are additional circuit connections to be identified in step 220, then the method 200 returns to step 205 and such circuit connections are identified. If all of the circuit connections are identified at step 220, then the first and second conduits of each of the identified circuit connections are connected at step 225. Once these circuit connections are made, the open RFID tags become active, and a set of data is received from each of the identified circuit connections from the active RFID tags in step 230. This is achieved by the conducting ring completing the open RFID tag as described above, and allowing the now active RFID tag to energize and send the set of data to the RFID reader. In step 235, the set of data from each of the identified circuit connections is analyzed, optimizing the ventilator 150 delivery based on the analysis, and the data is displayed along with the analysis and the optimization for a user. During step 235, alerts and/or reports may be provided to the user, and the user may manipulate the analysis such as with an override or turning off alarms, amending or closing the analysis accordingly.

Figure 5:
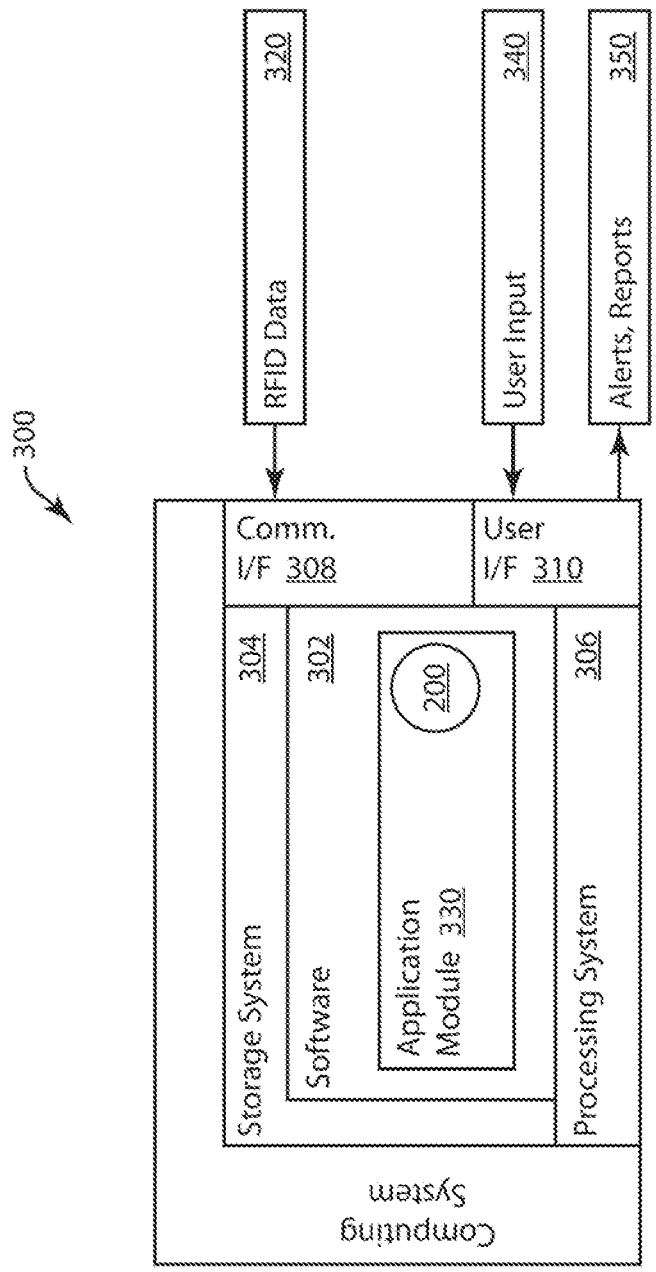
FIG. 5 is a block diagram illustrating an embodiment of the system of the present application.

FIG. 5 is a system diagram of an exemplary embodiment of a computing system 300 as may be used to implement embodiments of the method 200, or in carrying out embodiments of portions of the breathing circuit 100. The computing system 300 includes a processing system 306, storage system 304, software 302, communication interface 308, and a user interface 310. The processing system 306 loads and executes software 302 from the storage system 304, including a software module 330. When executed by the computing system 300, software module 330 directs the processing system to operate as described herein in further detail in accordance with the method 200, or a portion thereof. It should be noted that the computing system 300 may be configured in a number of locations proximate or remote from the breathing circuit 100. For example, the computing system 300 may be included in the ventilator 150 in the RFID reader 30, and/or in any user workstation proximate to the ventilator 150 or remote in a practitioner's station, care station, or other computer station.

Although the computing system 300 as depicted in FIG. 5 includes one application module 330 in the present example, it is to be understood that one or more modules could provide the same operations or that exemplary embodiments of the method 200 may be carried out by a plurality of modules 330. Similarly, while the description as provided herein refers to a computing system 300 and a processing system 306, it is to be recognized that implementations of such system can be performed by using one or more processors 306, which may be communicatively connected, and such implementations are considered with be within the scope of the description. Exemplarily, such implementations may be used in carrying out embodiments of the system 100 depicted in FIGS. 2 and 3.

Referring back to FIG. 5, the processing system 306 can comprise a microprocessor or other circuitry that retrieves and executes software 302 from storage system 304. Processing system 306 can be implemented within a single processing device but can also be distributed across multiple processing devices or sub-systems that cooperate in executing programming instructions. Examples of processing system 306 includes general purpose central processing units, application specific processor, and logic devices, as well as any other type of processing device, combinations of processing device, or variations thereof. The storage system 304 can include any storage media readable by the processing system 306 and capable of storing the software 302. The storage system 304 can include volatile and non-volatile, removable and non-removable media implemented in any method of technology for storage of information such as computer readable instructions, data structures, program modules or other data. Storage system 304 can be implemented as a single storage device but may also be implemented across multiple storage devices or sub-systems. Storage system 304 can further include additional elements, such as a controller capable of communicating with the processing system 306.

Examples of storage media include random access memory, read only memory, magnetic disc, optical discs, flash memory, virtual and non-virtual memory, magnetic sets, magnetic tape, magnetic disc storage or other magnetic storage devices or any other medium which can be used to store the desired information and that may be accessed by an instruction execution system, as well as any combination or variation thereof, or any other type of storage medium. In some implementations, the storage media can be a non-transitory storage media. It should be understood that in no case is the storage media propagated signal.

User interface 310 can include a mouse, a keyboard, a voice input device, a touch input device for receiving a gesture from a user, a motion input device for detecting non-touch gestures, and other motions by a user, and other comparable input devices and associated processing elements capable of receiving user input from a user. User interface 310 can also include output devices such as a video display or a graphical display that can display an interface associated with embodiments of the systems and methods as disclosed herein. Speakers, printers, haptic devices, and other types of output devices may also be included in the user interface 310. The user interface 310 is configured to receive user inputs 340 which in non-limiting embodiments may be irregularity user preferences as disclosed in further detail herein. It is also understood that embodiments of the user interface 310 can include a graphical display that presents the reports or alerts as described in further detail herein.

As has been described in further detail herein, the communication interface 308 is configured to receive RFID data 320. The RFID data 320, as described previously, may include the location of the circuit connection 10, the confirmation that a connection has indeed occurred, and any circuit component 135 that the corresponding active RFID tag 27 may be associated with. The computing system 300 processes the RFID data 320 according to the software 302 and as described in detail herein to produce reports and alerts 350 which may be pushed to one or more users through the user interface 310. The reports 250 may include any analysis conducted by the computing system including reports 350 on optimizing the ventilation delivery as described above. Further as described herein, the computing system 300 can output alerts, and/or report 350 to the user, and may further accept user input 340, such as but not limited to, setting off of alerts, modifications of the reports, and other administration of the alerts and data. It is the user interface 310, including the alert and reports 350 provided to the user and the user input 340 that allows response to a detection of a lapse in integrity of the breathing circuit 100 and may provide an alarm if a critical component is absence, or denies start of patient ventilation until a critical component is added or the denial is overridden by a user.

As described earlier, knowing the pairing of all the circuit components 135 and circuit connections 10 and the circuit connection 10 location of each circuit component 135, the arrangement of the entire breathing circuit 100 and circuit connections 10 can map out via the connected sequence of the paired active RFID tags 27 and rings 20. Along with the property of the circuit components 135, the fluid property of the breathing circuit 100 arrangement can be derived. For example, reading that the expiratory port 140 is connected to filter 135, that in turn is connected to the expiratory limb 115 and connected to an endotracheal tube 120, and knowing the flow resistance of each of the segments of the circuit elements 135, fluid resistance in the expiration limb 115 of the breathing circuit 100 can be computed and compensate the work of expired breathing by appropriately adjusting the ventilator 150 pressure during expiration in the control of the ventilation delivery. Likewise, in another example, knowing that an LMA 125 and filter 135 is connected to the common limb of the Y-piece 155 will help to determine the dead space ventilation contributed by the breathing circuit 100. The computing system 300 can therefore instruct the ventilator 150 to then compensate the increased dead space by correspondingly increasing the delivered tidal volume. In yet another compensation, the compliance of the connected circuit components 135 can be summed according to its serial or parallel connection to the gas flow path to compute the gas volume loss in the breathing circuit 100 and not delivered to the patient. To clarify, the computing system, in executing the method 200, may be able to instruct the ventilator 150 to correct integrity issues in the breathing circuit 100 found by the method 200.

While the invention has been described with reference to preferred embodiments, those skilled in the art will appreciate that certain substitutions, alterations and omissions may be made to the embodiments without departing from the spirit of the invention. Accordingly, the foregoing description is meant to be exemplary only, and should not limit the scope of the invention as set forth in the following claims.

In the foregoing description, certain terms have been used for brevity, clearness, and understanding. No unnecessary limitations are to be inferred therefrom beyond the requirement of the prior art because such terms are used for descriptive purposes and are intended to be broadly construed. The different configurations, systems, and method steps described herein may be used alone or in combination with other configurations, systems and method steps. It is to be expected that various equivalents, alternatives and modifications are possible within the scope of the appended claims.

What is claimed is:

1. A ventilator breathing circuit comprising:
a plurality of circuit connections, each of the plurality of circuit connections including a first conduit and a second conduit;
a radio frequency identification (RFID) reader;
an open RFID tag having an open state and a completed circuit state, wherein the open RFID tag is configured to be energized by the RFID reader only when the open RFID tag is in the completed circuit state, wherein the open RFID tag is only in the completed circuit state when the first conduit and the second conduit are connected, and wherein the open RFID tag is affixed to any of the first conduits;

a conducting ring affixed to the second conduit corresponding to the first conduit having the open RFID tag, wherein when the first conduit and the second conduit are connected, the conducting ring of the second conduit completes a circuit in the open RFID tag, changing the open RFID tag from the open state to the completed circuit state, wherein the open RFID tag is energized by the RFID reader and sends a set of data to the RFID reader, wherein the set of data includes information about the circuit connection.

2. The ventilator breathing circuit of claim 1, further comprising a ventilator, wherein the ventilator includes an expiratory port and an inspiratory port, each having the first or second conduit, wherein the RFID reader is physically configured in the ventilator.

3. The ventilator breathing circuit of claim 1, further comprising at least one circuit component, wherein the circuit component has a plurality of conduits, such that each of the plurality of conduits may be the first or second conduit.

4. The ventilator breathing circuit of claim 1, wherein the RFID reader sends the set of data to a computing system, such that the computing system processes the set of data and analyzes the set of data, and produces a report based on the analysis.

5. The ventilator breathing circuit of claim 4, wherein the computing system further processes the RFID data and optimizes a delivery of the ventilator.

6. The ventilator breathing circuit of claim 5, wherein the computing system displays the set of data and the analysis for a user.

7. The ventilator breathing circuit of claim 5, wherein the computing system displays the optimization of the delivery of the ventilator for the user.

8. The ventilator breathing circuit of claim 1, further comprising a patient interface component having an interface conduit such that the interface conduit may be the first and second conduit.

9. A method of monitoring the integrity of a ventilator breathing circuit, the method comprising:
    identifying a circuit connection of a the ventilator breathing circuit;
    fashioning a first conduit of the circuit connection with an open RFID tag, wherein the open RFID tag has an open state and a completed circuit state, wherein the open RFID tag is configured to be energized only in the completed circuit state, wherein the open RFID tag is only in the completed circuit state when the first and second conduits of the identified circuit connection are connected;
    fashioning a second conduit of the circuit connection with a conducting ring;
    connecting the first and second conduits of the identified circuit connection, thus changing the open RFID tag from the open state to the completed circuit state and also energizing the open RFID tag;
    receiving a set of data from the identified circuit connection; and
    analyzing the set of data from the identified circuit connection and
    displaying the analysis for a user.

10. The method of claim 9, wherein the set of data is received from the identified circuit connection with a radio frequency identification (RFID) reader.

11. The method of claim 9, wherein the set of data includes information about the circuit connection.

12. The method of claim 9, wherein when the first conduit and the second conduit are connected, the conducting ring of the second conduit completes a circuit in the open RFID tag, changing the open RFID tag from the open state to the completed circuit state.

13. The method of claim 9, wherein a ventilator includes an expiratory port and an inspiratory port, each having the first or second conduit, and physically configuring the RFID reader in the ventilator.

14. The method of claim 9, wherein at least one circuit component has a plurality of conduits, such that each of the plurality of conduits may be the first or second conduit.

15. The method of claim 9, wherein a patient interface component has an interface conduit such that the interface conduit may be the first and second conduit.

16. The method of claim 9, further comprising the RFID reader sending the set of data to a computing system, such that the computing system processing the set of data, analyzes the set of data, and optimizing a delivery of the ventilator based on the analysis.

17. The method of claim 16, further comprising displaying the analysis and optimization for a user.

18. A non-transitory computer-readable medium including instructions that, when executed on a computing system, cause the computing system to:
    receive a set of data from a circuit connection wherein an open RFID tag having an open state and a completed circuit state and configured to be energized only when in the completed circuit state is changed from the open state to the completed circuit state and also energized by a conducting ring when a connection is made between a first and second conduit;
    analyze the set of data from the circuit connection;
    optimize a delivery of the ventilator based on the analysis; and
    display the analysis and the optimization for a user.

* * * * *